(12) United States Patent
Kobayashi et al.

(10) Patent No.: US 11,565,099 B2
(45) Date of Patent: Jan. 31, 2023

(54) MICRONEEDLE ARRAY, SUPPORT MEMBER, METHOD OF PRODUCING MICRONEEDLE ARRAY, AND MICRONEEDLE ARRAY UNIT

(71) Applicant: FUJIFILM Corporation, Tokyo (JP)

(72) Inventors: Yuka Kobayashi, Kanagawa (JP); Yoshiki Sakazaki, Kanagawa (JP); Kenichiro Tamaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 247 days.

(21) Appl. No.: 17/019,368

(22) Filed: Sep. 14, 2020

(65) Prior Publication Data

US 2021/0085943 A1   Mar. 25, 2021

(30) Foreign Application Priority Data

Sep. 25, 2019 (JP) .............................. JP2019-174153

(51) Int. Cl.
*A61M 37/00* (2006.01)
(52) U.S. Cl.
CPC . *A61M 37/0015* (2013.01); *A61M 2037/0023* (2013.01); *A61M 2037/0053* (2013.01); *A61M 2209/06* (2013.01); *A61M 2209/08* (2013.01)
(58) Field of Classification Search
CPC ...... A61M 37/0015; A61M 2037/0023; A61M 2037/0053; A61M 2209/06;
(Continued)

(56) References Cited

U.S. PATENT DOCUMENTS 6,322,808 B1   11/2001 Trautman, et al.
2007/0083151 A1   4/2007 Carter
(Continued)

FOREIGN PATENT DOCUMENTS

EP   2835147      2/2015
JP   2017070390   4/2017
(Continued)

OTHER PUBLICATIONS

"Search Report of Europe Counterpart Application", dated Apr. 22, 2021, p. 1-p. 6.

(Continued)

*Primary Examiner* — Amber R Stiles
(74) *Attorney, Agent, or Firm* — JCIPRNET

(57) ABSTRACT

The present invention provides a microneedle array, a support member, a method of producing a microneedle array, and a microneedle array unit which enable reduction of a drying time during production and prevention of breakage during drying.

Provided are a microneedle array 120 including a sheet portion 41, a plurality of needle-like protrusions 44, and a support member 50 formed of a gripping portion 52 and a beam portion 54 having one end that is connected to the gripping portion 52, in which the sheet portion 41 is an integrally molded body which is integrally molded with the support member 50, in which at least a part of the beam portion 54 is buried under the other surface 43 of the sheet portion 41, opposite to the one surface where the needle-like protrusions 44 are provided, the gripping portion 52 is provided on the other surface 43 of the sheet portion 41, and the beam portion 54 is deformable toward a center of the sheet portion 41. Further, provided are the support member 50, a method of producing the microneedle array 120, and a microneedle array unit 300 including a container 310.

13 Claims, 15 Drawing Sheets

(58) Field of Classification Search
CPC ...... A61M 2209/08; A61M 2037/0046; A61M 2037/003; B29L 2031/7544; B29L 2031/756; B29C 39/025; B29C 39/026; B29C 39/10; B29C 39/26
See application file for complete search history.

(56) References Cited

U.S. PATENT DOCUMENTS

| | | |
|---|---|---|
| 2011/0152792 A1 | 6/2011 | Takada |
| 2016/0354589 A1 | 12/2016 | Kobayashi et al. |
| 2017/0095427 A1 | 4/2017 | Wakamatsu |
| 2021/0023355 A1* | 1/2021 | Tamaki ............. A61M 37/0015 |

FOREIGN PATENT DOCUMENTS

| | | |
|---|---|---|
| KR | 20190107538 | 9/2019 |
| WO | 2010140401 | 12/2010 |

OTHER PUBLICATIONS

"Search Report of Europe Counterpart Application", dated Nov. 28, 2022, pp. 1-7.

* cited by examiner

FIG. 22
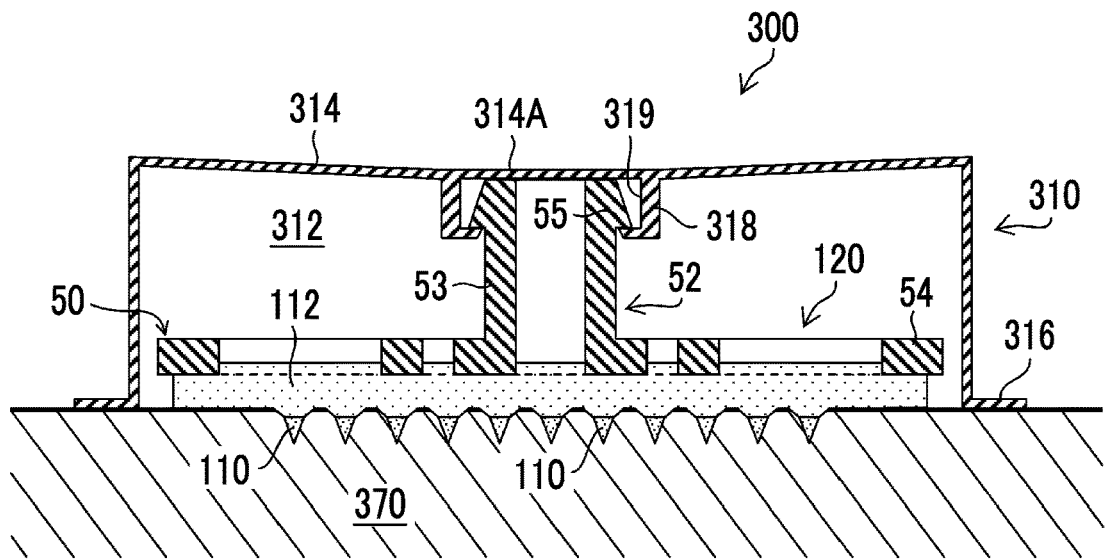
FIG. 23
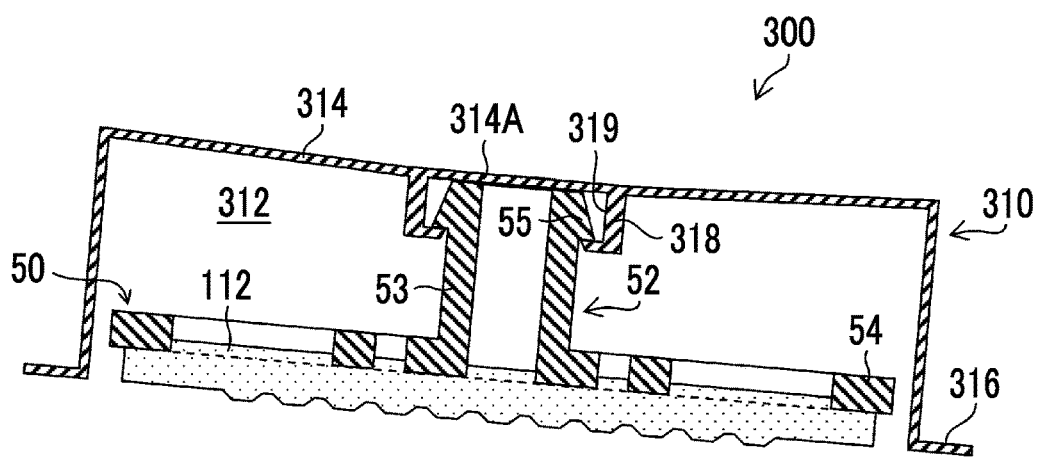
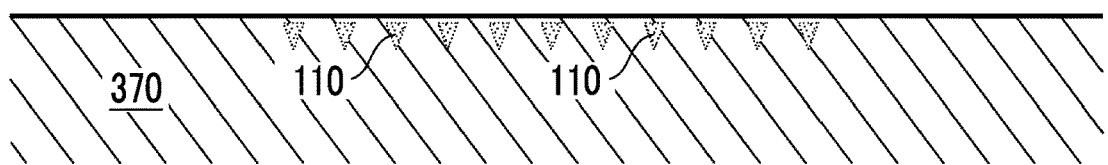

MICRONEEDLE ARRAY, SUPPORT MEMBER, METHOD OF PRODUCING MICRONEEDLE ARRAY, AND MICRONEEDLE ARRAY UNIT

CROSS-REFERENCE TO RELATED APPLICATIONS

The present application claims priority under 35 U.S.C § 119 to Japanese Patent Application No. 2019-174153 filed on Sep. 25, 2019. The above application is hereby expressly incorporated by reference, in its entirety, into the present application.

BACKGROUND OF THE INVENTION

1. Field of the Invention

The present invention relates to a microneedle array, a support member, a method of producing a microneedle array, and a microneedle array unit and particularly relates to a microneedle array attached to a container and a puncture device, a support member, a method of producing a microneedle array, and a microneedle array unit.

2. Description of the Related Art

In recent years, a microneedle array (micro-needle array) has been known as a new dosage form that enables administration of drugs such as insulin, vaccines, and human growth hormones (hGH) into the skin without pain. Each microneedle of a microneedle array is pierced into the skin by attaching biodegradable microneedles containing a drug to the skin, and these microneedles are absorbed in the skin so that the drug contained in each microneedle is administered into the skin.

In order to use a microneedle array safely and conveniently, it is desired that a user can perform a treatment directly without holding the microneedle array by hand by attaching the microneedle array to a container or a puncture device.

As one method of attaching a microneedle array to a container or a puncture device, a method of integrally molding a support with a microneedle array in a case of molding the microneedle array and attaching the microneedle array to a container or a puncture device using this support is performed. For example, JP2017-070390A describes that a sheet portion of a transdermal absorption sheet has a sheet-like mesh structure. WO2010/140401A describes a microneedle array formed by bringing a porous support into contact with the surface of a base material liquid before a step of drying the base material liquid and impregnating the porous support with the base material liquid so that the support and the microneedle array are integrated with each other.

SUMMARY OF THE INVENTION

However, since the mesh structure used in the transdermal absorption sheet described in JP2017-070390A is formed in a lattice shape, the mesh structure does not contract even in a case where the microneedle array contracts due to drying. Therefore, there is a problem in that the microneedle array is broken and damaged. Further, as in the microneedle array described in WO2010/140401A, there is a problem in that it takes time to dry the base material liquid in a case where the support is brought into contact with the surface of the base material liquid.

Further, as another method of attaching a microneedle array to a container and a puncture device, a method of providing a mechanism in which a microneedle array is fixed with a pressure sensitive adhesive or a mechanism in which a microneedle array is held by a container and a puncture device is performed. However, in a case where a microneedle array is fixed the pressure sensitive adhesive, components of the pressure sensitive adhesive are eluted to the microneedle array. Accordingly, there is a concern of safety for a living body. Further, in a case where the mechanism in which the microneedle array is held by a container and a puncture device is provided, the structures of the container and the puncture device are complicated. Accordingly, there is a concern that the cost increases and puncture properties are impaired due to the holding mechanism.

The present invention has been made in consideration of the above-described circumstances, and an object of the present invention is to provide a microneedle array, a support member, a method of producing a microneedle array, and a microneedle array unit which enable reduction of a drying time and prevention of breakage of the microneedle array during drying even in a case where a support mounted on a container or a puncture device is integrally molded with the microneedle array.

In order to achieve the object of the present invention, there is provided a microneedle array comprising: a sheet portion; a plurality of needle-like protrusions arranged on one surface of the sheet portion; and a support member formed of a gripping portion which extends in one direction and a beam portion having one end that is connected to the gripping portion, in which the sheet portion is an integrally molded body which is integrally molded with the support member, in which at least a part of the beam portion is buried under the other surface of the sheet portion, opposite to the one surface where the needle-like protrusions are provided, the gripping portion is provided on the other surface of the sheet portion, and the beam portion is deformable toward a center of the sheet portion.

In order to achieve the object of the present invention, there is provided a support member which supports a sheet portion of a microneedle array, the support member comprising: a gripping portion which extends in one direction; and a beam portion having one end that is connected to a side surface of the gripping portion and curvedly extending from the gripping portion in a diametric direction and a circumferential direction, in which the beam portion is deformable toward the gripping portion.

In order to achieve the object of the present invention, there is provided a method of producing a microneedle array, comprising in the following order: a polymer-dissolved solution filling step of supplying a polymer-dissolved solution to a pattern surface of a mold having needle-like depressions and filling the needle-like depressions with the polymer-dissolved solution; a support member placing step of placing the support member described above on the mold from above the polymer-dissolved solution applied onto the needle-like depressions; a polymer layer forming step of drying the polymer-dissolved solution such that a polymer layer and the support member are integrally molded with each other; and a peeling step of peeling the polymer layer and the support member from the mold.

In order to achieve the object of the present invention, there is provided a method of producing a microneedle array, comprising in the following order: a drug solution filling step of filling a pattern surface of a mold with a drug solution containing a drug; a drug layer forming step of drying the drug solution to form a drug layer; a base material liquid filling step of filling the drug layer with a base material liquid; a support member placing step of placing the support member according to any one of claims 6 to 10 on the mold from above the base material liquid filling the drug layer; a base material layer forming step of drying the base material liquid such that a base material layer and the support member are integrally molded with each other; and a peeling step of peeling the drug layer, the base material layer, and the support member from the mold.

In order to achieve the object of the present invention, there is provided a microneedle array unit comprising: the microneedle array described above; and a container which accommodates the microneedle array, in which the container includes an accommodation portion having an opening, a deformable portion disposed on a side opposite to the opening and formed integrally with the accommodation portion, a binding portion provided in the accommodation portion of the deformable portion and bound to the gripping portion of the microneedle array, and a lid member which seals the opening, the binding portion of the container is fitted and bound to the gripping portion of the microneedle array, the deformable portion is deformed by receiving an external force in a direction of the opening and presses the microneedle array through the gripping portion, the microneedle array is pushed out of the accommodation portion by being pressed, and the deformable portion maintains a deformed state and presses the microneedle array.

According to the present invention, in a case where the beam portion of the support member is made to be deformable toward the center of the sheet portion, the beam portion can be deformed by following contraction of the sheet portion in a case of drying the sheet portion in the production of the microneedle array. Therefore, it is possible to prevent breakage of the sheet portion due to the drying. Further, the opening portion of the support member can be enlarged by forming the support member with the beam portion in a case of drying the sheet portion, and thus it is possible to prevent the drying from being inhibited even in a case where the support member is disposed. In addition, the support member can be integrally molded with the microneedle array so that the microneedle array can be attached to a container or a puncture device using the gripping portion of the support member, and thus a user can use the microneedle array safely and conveniently without directly touching the sheet portion and the needle-like protrusions.

BRIEF DESCRIPTION OF THE DRAWINGS

FIG. 22 is a view for describing a step of puncturing the skin with a microneedle array.

FIG. 23 is a view for describing a step of puncturing the skin with a microneedle array.

DESCRIPTION OF THE PREFERRED EMBODIMENTS

Hereinafter, a microneedle array and a microneedle array unit according to the embodiment of the present invention will be described with reference to the accompanying drawings.

[Method of Producing Microneedle Array]

Figure 1:
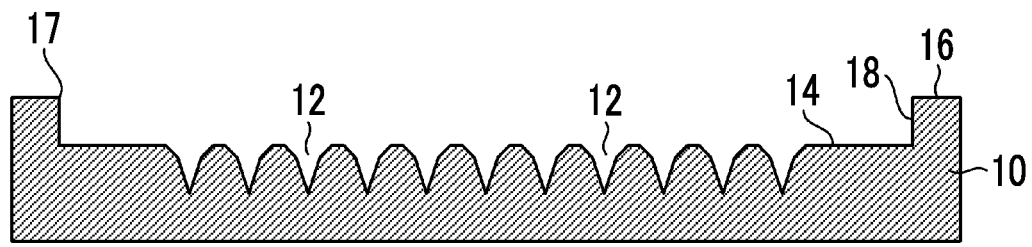
FIG. 1 is a step view illustrating a procedure for producing a microneedle array.

FIGS. 1 to 7 are step views illustrating a procedure for producing a microneedle array. In the production of the microneedle array, first, a mold 10 having needle-like depressions 12 is prepared as illustrated in FIG. 1. For example, the mold 10 can be produced by performing the following steps.

In production of the mold 10, a first mold is formed by performing imprint on a resin precursor from a precursor on which a projection pattern corresponding to needle-like protrusions of a microneedle array to be produced is formed. A duplicate mold is formed by performing an electroforming treatment after the formation of the first mold. Next, a mold sheet having needle-like depressions 12, which is a reverse type of the duplicate mold, is formed using a resin film from the duplicate mold. Finally, the mold 10 having needle-like depressions is formed by punching the mold sheet and then cutting the mold sheet for each pattern.

As the material of the mold 10, a medical grade silicone material (such as MDX-4210, manufactured by Dow Corning Corp.), a UV curable resin which is cured by irradiation with ultraviolet rays, or a plastic resin such as polystyrene or polymethyl methacrylate (PMMA) can be used.

Figure 2:
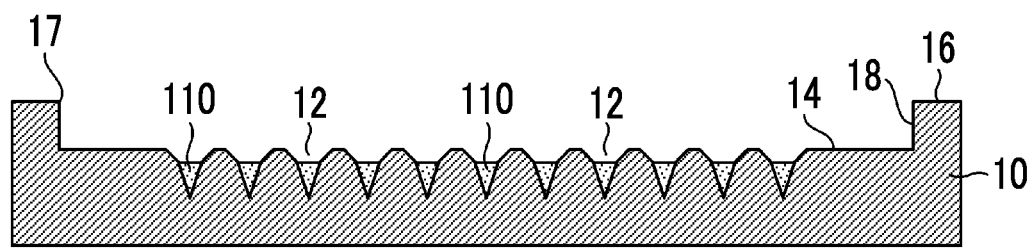
FIG. 2 is a step view illustrating a procedure for producing a microneedle array.

Next, as illustrated in FIG. 2, a drug layer 110 containing a drug in the needle-like depressions 12 is formed (drug layer forming step) by supplying a drug solution to the needle-like depressions 12 (drug solution filling step) and drying the drug solution. The drug layer 110 is formed by coating a region 14 (pattern surface) where the needle-like depressions 12 have been formed with the drug solution containing the drug. The coating method is not particularly limited and, for example, the coating can be performed by supplying the drug solution through a nozzle. Further, a spot deposition method may be used. After the supply of the drug solution, the drug solution can be sucked from the rear surface of the mold 10, and the filling of the needle-like depressions 12 with the drug solution can be accelerated.

After the needle-like depressions 12 are filled with the drug solution, the drug solution is dried to form the drug layer 110. The drug is dried by controlling the temperature and humidity conditions to optimize the drying speed so that adhesion of the drug solution to the wall surface of the needle-like depressions 12 can be reduced, and the drying can be promoted while the drug solution is collected at the tips of the needle-like depressions 12 by drying the drug solution.

By drying the drug solution, the drug solution is solidified and can be more contracted than the drug solution in a state of filling the needle-like depressions. In this manner, the drug layer 110 can be easily peeled off from the needle-like depressions 12 in a case of peeling the microneedle array 120 from the mold 10.

Figure 3:
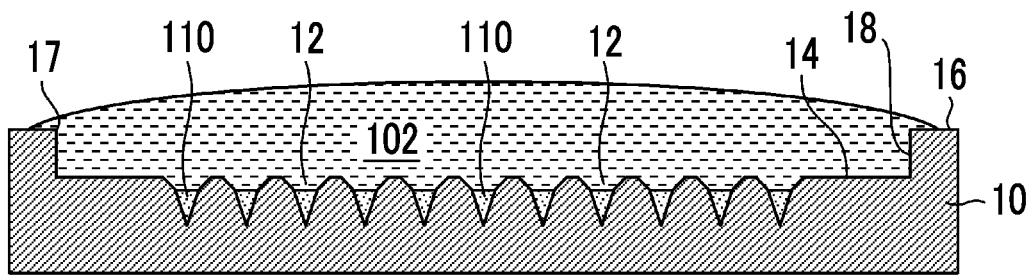
FIG. 3 is a step view illustrating a procedure for producing a microneedle array.

Next, as illustrated in FIG. 3, a base material liquid 102 is supplied onto the drug layer 110 containing a predetermined amount of the drug, and the base material liquid 102 is supplied onto the needle-like depressions 12 and the region 14 where the needle-like depressions 12 have been formed (base material liquid filling step). The base material liquid 102 is a polymer-dissolved solution that forms the base material layer 112. The base material liquid 102 can be supplied by coating the region with the base material liquid using a dispenser or coating the region with the base material liquid according to a spot deposition method, but the present invention is not limited thereto. Since the drug layer 110 is solidified by drying the liquid, diffusion of the drug contained in the drug layer 110 into the base material liquid 102 can be suppressed.

Figure 4:
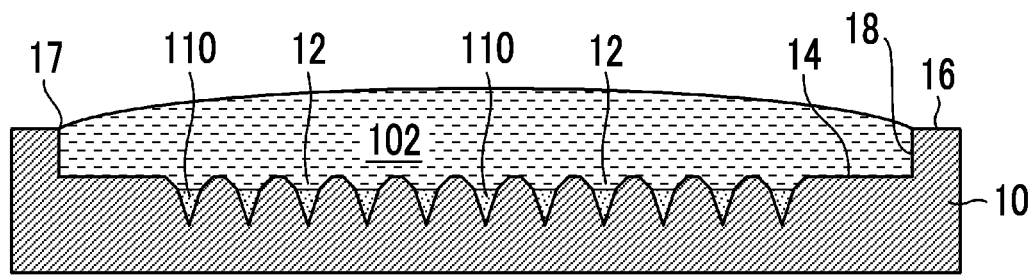
FIG. 4 is a step view illustrating a procedure for producing a microneedle array.

As illustrated in FIG. 3, the supply of the base material liquid 102 is carried out such that at least a part of a stepped portion 16 provided in the periphery of the region 14 where the needle-like depressions 12 have been formed is covered with the base material liquid 102. Further, the base material liquid 102 is supplied beyond a contact position 17 from a side of the region 14 where the needle-like depressions 12 have been formed. The supplied base material liquid 102 is repelled by the mold 10 and contracts due to the surface tension. As illustrated in FIG. 4, the contracted base material liquid 102 is fixed (pinned) at the contact position 17 which is a contact point between the stepped portion 16 of the mold 10 and a wall portion 18 formed from the region 14 where the needle-like depressions 12 have been formed toward the stepped portion 16. After the base material liquid 102 is supplied, vacuum suction may be performed from a side of the mold 10 opposite to the region 14 where the needle-like depressions 12 have been formed. By performing the vacuum suction, the needle-like depressions 12 can be filled with the base material liquid 102. Further, in a case where bubbles are present in the base material liquid 102, the bubbles can be removed by suction.

Figure 5:
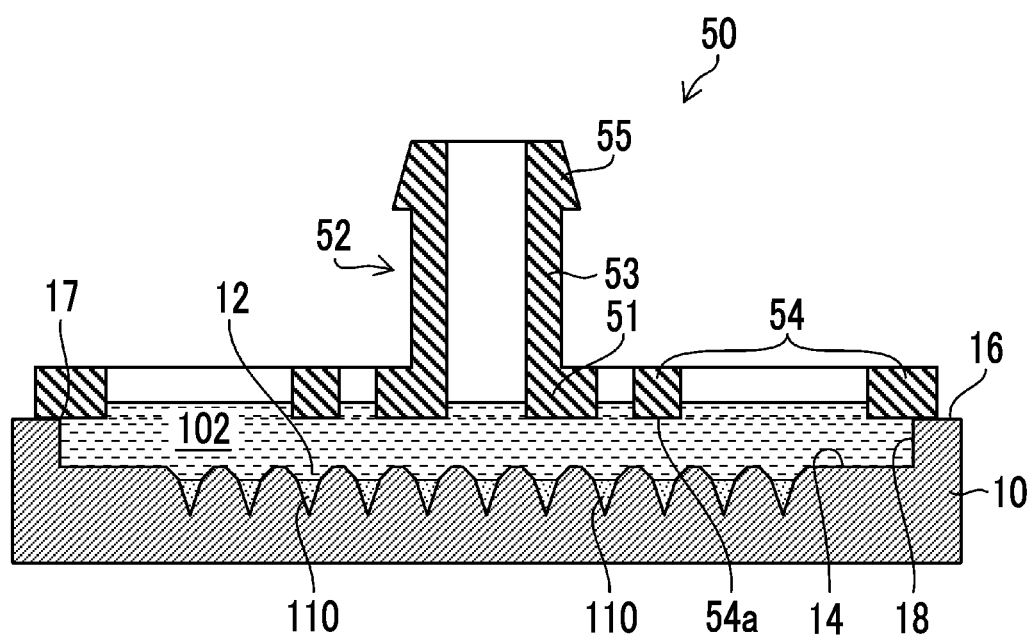
FIG. 5 is a step view illustrating a procedure for producing a microneedle array.
Figure 8:
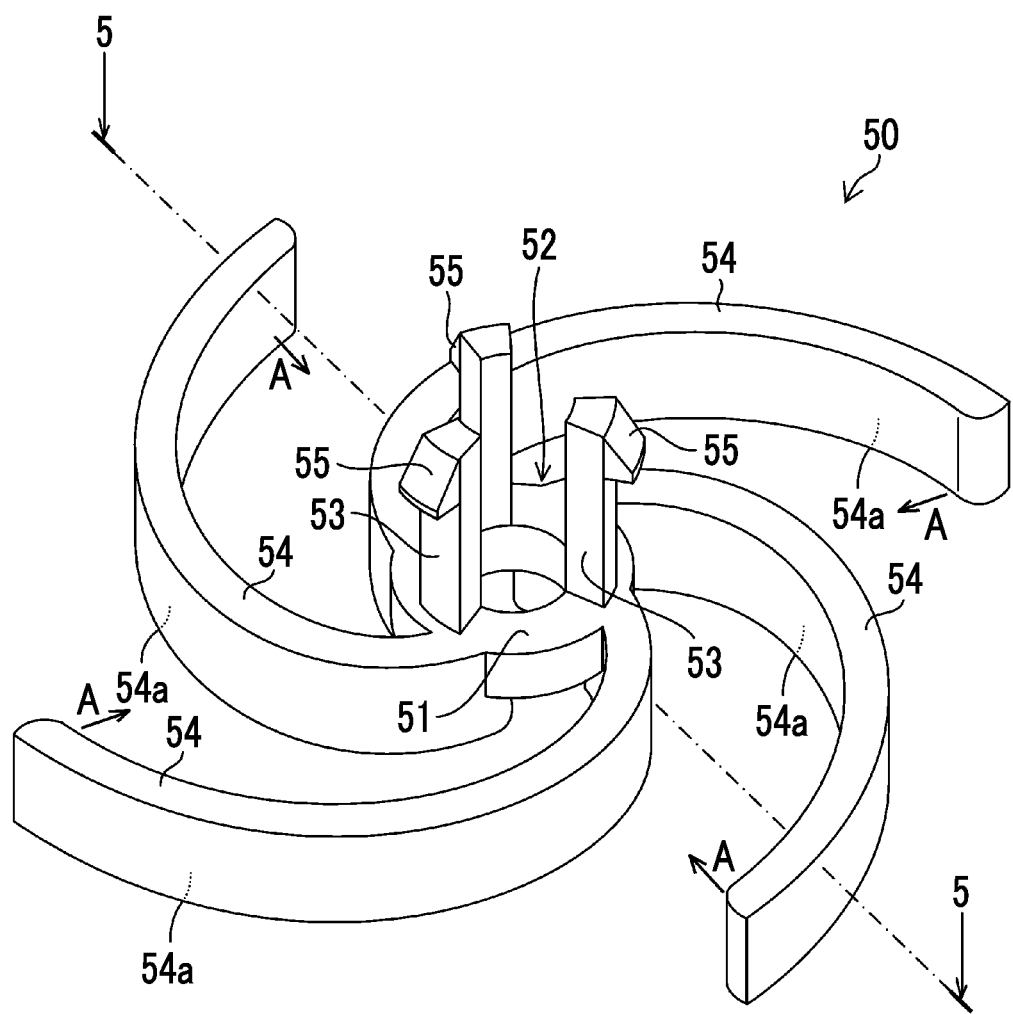
FIG. 8 is a perspective view of a support member.

Next, as illustrated in FIG. 5, the support member 50 is placed on the stepped portion 16 of the mold 10 from above the base material liquid 102 supplied onto the mold 10 (support member placing step). FIG. 8 is a perspective view illustrating the support member 50. The support member 50 comprises a gripping portion 52 that extends in one direction and a beam portion 54 having one end that is connected to a side surface of the gripping portion 52. The gripping portion 52 comprises a circular base portion 51 and a rod-like portion 53 formed in a direction (one direction) perpendicular to a circular surface of the base portion 51. The end of the rod-like portion 53 on a side opposite to the base portion 51 has a claw portion 55 that fits into a container in a case of storing the microneedle array in the container and fixing the microneedle array thereto. The beam portion 54 is formed such that one end thereof is connected to a side surface of the base portion 51 and curvedly extends from the gripping portion 52 in the diametric direction and the circumferential direction. In FIG. 8, the gripping portion 52 extends in a radial direction with the gripping portion 52 as the center and is curved in a circumferential direction. The beam portion 54 can be deformed in the direction (the direction toward the gripping portion 52) indicated by an arrow A shown in the figure by providing the beam portion 54 so as to be curved in the circumferential direction. Further, since the beam portion 54 can be deformed by following contraction due to drying of the base material liquid 102 in the drying of the base material liquid described below by providing the beam portion 54 so as to be curved in the circumferential direction, it is possible to prevent breakage (breakage of the base material layer) due to the drying of the base material liquid 102. Further, as illustrated in FIG. 5, since the beam portion 54 is placed on the stepped portion 16 of the mold 10, the support member 50 is provided such that the other end of the beam portion 54 is positioned outside the region 14 where the needle-like depressions 12 have been formed in a case of placing the support member 50 on the mold 10. In addition, the cross section of the support member 50 illustrated in FIG. 5 is a cross section taken along the line 5-5 shown in FIG. 8.

FIG. 8 illustrates a configuration in which the base portion 51 comprises three rod-like portions 53, but the present invention is not limited thereto. Further, a configuration in which the claw portion 55 is provided at the end by increasing the columnar shape of the base portion 51 without providing the rod-like portion 53 can be employed. Further, the shape of the base portion 51 is not limited to the circular shape, and a triangular shape or a further polygonal shape can be employed.

As illustrated in FIG. 4, the base material liquid 102 is held at a position higher than the stepped portion 16 due to the surface tension. In this state, at least a part of the beam portion 54, that is, a lower end 54a of the beam portion 54 can be buried by placing the support member 50 on the stepped portion 16 of the mold 10.

As the material constituting the support member 50, a drug product application grade cycloolefin polymer (COP) can be used. Alternatively, a resin such as polyethylene or polypropylene can be used. Further, a metal can be used.

Figure 6:
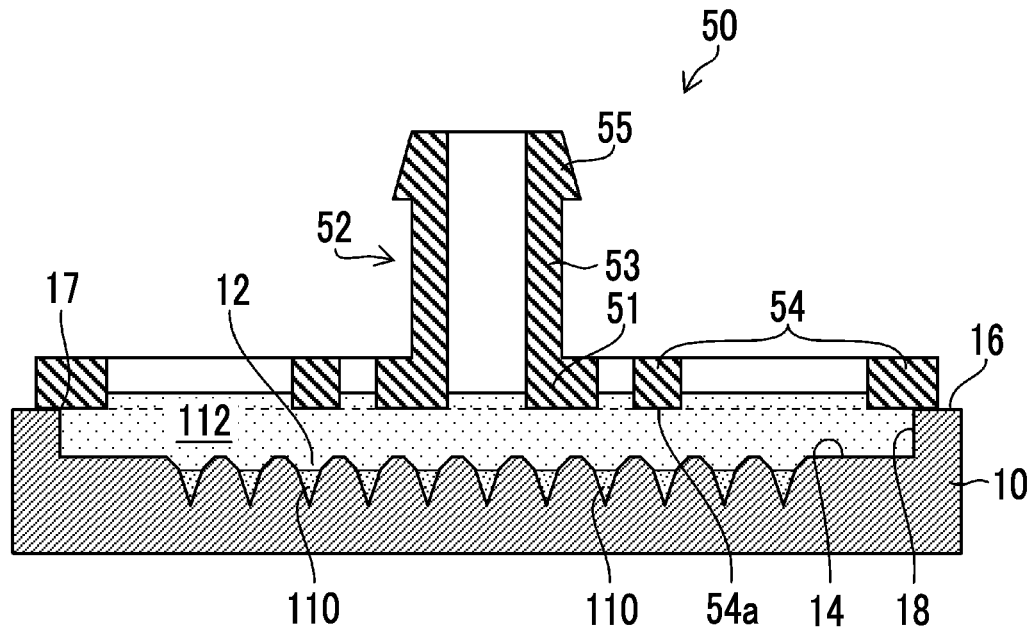
FIG. 6 is a step view illustrating a procedure for producing a microneedle array.

Returning to FIG. 6, the base material liquid 102 is dried and solidified (base material layer forming step) after the support member 50 is placed on the stepped portion 16 of the mold 10. In this manner, as illustrated in FIG. 6, the base material layer 112 can be formed on the drug layer 110 so that the microneedle array 120 having the drug layer 110 and the base material layer 112 is formed. According to the support member 50 of the present embodiment, since there is a gap between the beam portions 54, it is possible to prevent the delay in drying even in a case of placing the support member 50. Further, in a case where the base material liquid 102 is dried and solidified to form the sheet portion, an integrally molded body formed by molding the support member 50 and the sheet portion integrally with each other can be obtained. The tip of the gripping portion 52 is provided so as to be exposed from a side of the base material layer 112 opposite to the surface on which the drug layer 110 has been formed. In this manner, the end thereof can be fixed to the binding portion 318 of the container 310 described below.

The base material liquid 102 contracts toward the center of the applied base material liquid 102. In a case of placing the support member 50, the support member 50 is placed such that the gripping portion 52 is positioned at the center of the applied base material liquid 102, that is, at the center of the region 14 of the mold 10 where the needle-like depressions 12 have been formed. In this manner, the base material liquid 102 contracts toward the gripping portion 52 of the support member 50. Since the beam portion 54 is formed by being curved in the circumferential direction and is deformable toward the gripping portion 52, the beam portion 54 is deformable toward the center of the base material liquid 102, that is, the center of the dried sheet portion. As described above, by allowing the beam portion 54 to be further curved by following contraction of the base material liquid 102 in a case of contraction of the base material liquid 102, it is possible to prevent breakage of the base material layer in a case of drying the base material liquid 102.

In the beam portion 54 of the support member 50 and the base material layer 112, the contraction force that the base material liquid 102 contracts due to the drying of the base material liquid 102 and the restoring force that the beam portion 54 followed by the contraction force is expected to return to the original state interact with each other so that the support member 50 and the base material layer 112 are integrally molded with each other. Further, fine depressions and protrusions to be molded during the production of the support member 50, projections, and the like are formed on the surface of the beam portion 54. The support member 50 and the base material layer 112 can be fixed by the anchor effect in which the base material liquid 102 enters between the fine depressions and protrusions, projections, and the like.

The moisture content and the like of the microneedle array 120 due to the drying are set as appropriate. Further, in a case where the moisture content of the base material layer 112 is extremely small due to the drying, since the microneedle array is unlikely to be peeled off, it is preferable that the moisture content in a state where the elastic force is maintained is allowed to remain.

Figure 7:
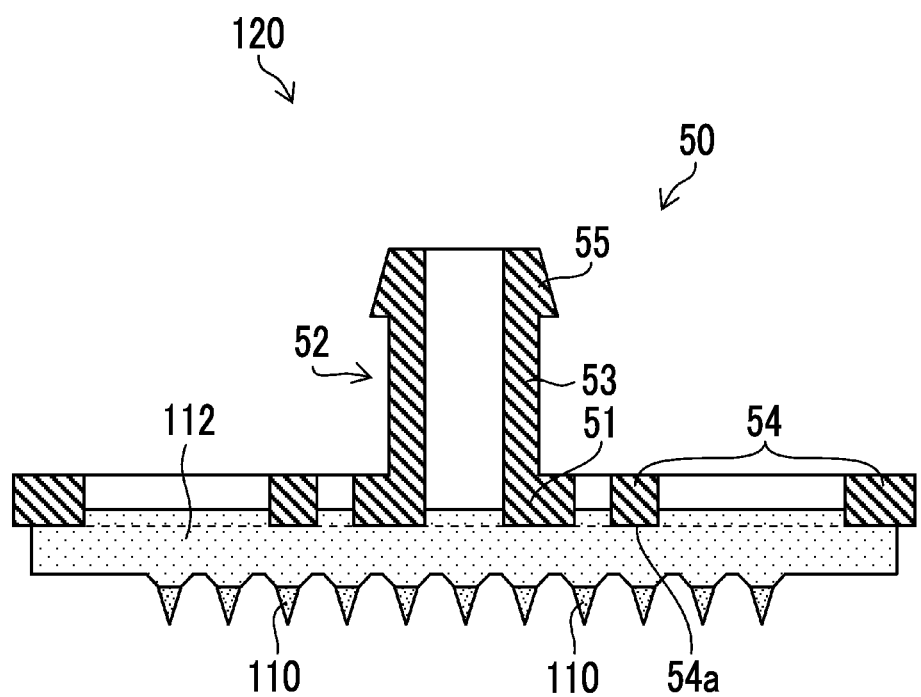
FIG. 7 is a step view illustrating a procedure for producing a microneedle array.

Finally, as illustrated in FIG. 7, the microneedle array 120 is produced by peeling the dried microneedle array 120 off from the mold 10 (peeling step).

Figure 9:
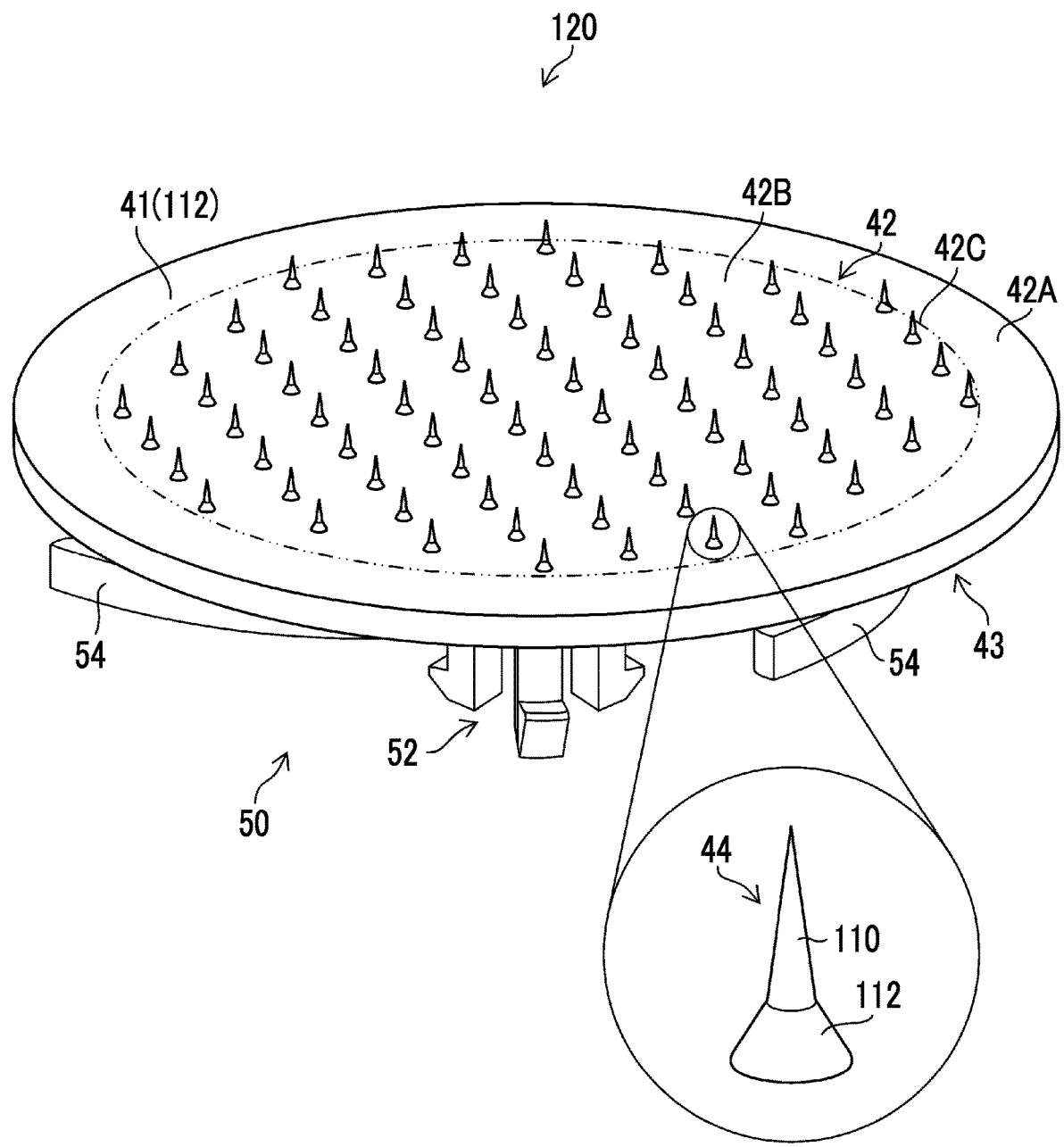
FIG. 9 is a perspective view of a microneedle array.

FIG. 9 is a perspective view of the microneedle array as viewed from a side of the needle-like protrusion 44. The produced microneedle array to be produced comprises a sheet portion 41 formed of the base material layer 112, and a plurality of needle-like protrusions 44 arranged on one surface 42 of the sheet portion 41. In the needle-like protrusion 44, the tip thereof is formed of the drug layer 110 and the base end thereof is formed of the base material layer 112. The needle-like protrusion 44 forms a microneedle. The plurality of needle-like protrusions 44 are arranged in a microneedle region 42B inside an outer peripheral surface 42A of the one surface 42. As illustrated in FIG. 9, the boundary between the outer peripheral surface 42A and the microneedle region 42B is an imaginary line 42C connecting the outermost needle-like protrusions 44 among the plurality of needle-like protrusions 44.

The shapes and the dimensions of the sheet portion 41 and the needle-like protrusion 44 may be selected depending on the applications of the microneedle array 120. In the embodiment, the example in which the sheet portion 41 has a circular shape has been described, but the sheet portion 41 may have a rectangular shape.

The needle-like protrusion 44 has a substantially conical shape, but the needle-like protrusion 44 may have a columnar shape, a frustum shape, or the like. In the embodiment, the needle-like protrusion 44 is formed in order of a truncated cone portion and a cone from the one surface 42 toward the tip, but is not particularly limited as long as the skin can be punctured by the needle-like protrusion. It is preferable that the needle-like protrusions 44 are arranged in an array in a state where columns (lateral line) and rows (horizontal line) are uniformly spaced.

The sheet portion 41 of the microneedle array 120 has a diameter of, for example, 10 mm to 30 mm. Further, the needle-like protrusion 44 has a length of, for example, 0.2 mm to 1.5 mm. Further, for example, 4 to 1000 needle-like protrusions 44 are arranged on one surface 42 of the sheet portion 41. However, the present invention is not limited to these values.

The gripping portion 52 of the support member 50 is provided to protrude on a side of the other surface 43 of the microneedle array 120. The gripping portion 52 functions as a fitted portion to which the binding portion 318 provided on a deformable portion 314 of the container 310 described below is fitted. Further, in a case where the microneedle array 120 is handled by using the gripping portion 52, since it is possible to prevent the user from directly holding the needle-like protrusions 44 of the microneedle array 120 and the one surface 42 of the sheet portion 41 by hand, the microneedle array 120 can be used safely and conveniently.

[Base Material Liquid]

The base material liquid which is a solution in which a polymer resin used in the present embodiment has been dissolved will be described.

As the material of the resin polymer used in the base material liquid, it is preferable to use a resin with biocompatibility. Preferred examples of such resins include saccharides such as glucose, maltose, pullulan, chondroitin sulfate, sodium chondroitin sulfate, sodium hyaluronate, and hydroxyethyl starch; proteins such as gelatin; and biodegradable polymers such as polylactic acid and a lactic acid-glycolic acid copolymer. Although the concentration varies depending on the material, it is preferable that the concentration of the resin polymer in the base material liquid is set to be in a range of 10% by mass to 50% by mass. Further, the solvent used for dissolution may be any solvent other than warm water as long as it has volatility, and methyl ethyl ketone (MEK), alcohol, or the like can be used.

In a case where a water-soluble polymer (such as gelatin) is used, the base material liquid can be prepared by dissolving water-soluble powder in water. In a case where the water-soluble powder is unlikely to be dissolved in water, dissolution may be performed by heating water. The temperature can be appropriately selected depending on the kind of the polymer material, but it is preferable to heat water at a temperature of approximately 60° C. or lower. The viscosity of the base material liquid is preferably 2000 Pa·s or less and more preferably 1000 Pa·s or less. By appropriately adjusting the viscosity of the base material liquid, the base material liquid can be easily injected into the needle-like depressions of the mold. The viscosity of the base material liquid can be measured by, for example, a capillary viscometer, a falling ball viscometer, a rotary viscometer, or a vibration viscometer.

Drug Solution

The drug solution forming the drug layer 110 will be described. The drug solution is a solution in which the base material liquid contains a predetermined amount of drug. Whether or not the base material liquid includes a predetermined amount of drug is determined based on whether or not a drug effect can be exhibited at the time of puncturing the body surface. Therefore, the expression "including a predetermined amount of drug" indicates that the base material liquid contains the drug in an amount that enables exhibition of the drug effect at the time of puncturing the body surface.

The drug contained in the drug solution is not limited as long as the drug has a function as a drug. In particular, it is preferable that the drug is select from peptides, proteins, nucleic acids, polysaccharides, vaccines, pharmaceutical compounds belonging to water-soluble low-molecular-weight compounds, and cosmetic components.

The concentration of the polymer in the drug solution (the concentration of the polymer excluding the drug in a case where the drug itself is the polymer) is preferably in a range of 0% by mass to 30% by mass. Further, the viscosity of the drug solution is preferably 100 Pa·s or less and more preferably 10 Pas or less.

[Another Method of Producing Microneedle Array]

FIGS. 10 to 13 are step views illustrating another method of producing a microneedle array. Even in the production method according to the present embodiment, first, the mold 10 having the needle-like depressions 12 is prepared.

Figure 10:
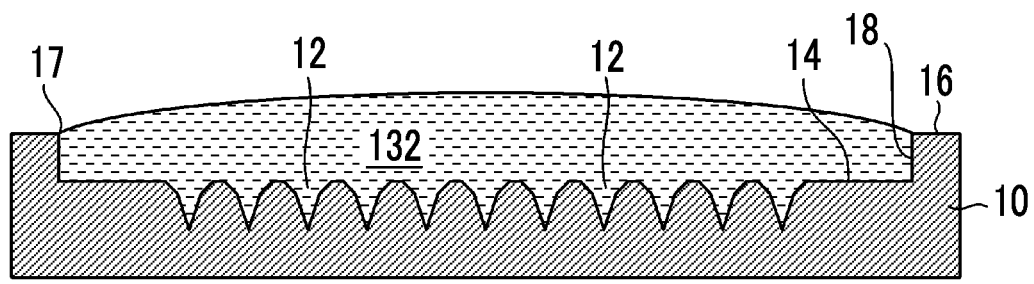
FIG. 10 is another step view illustrating a procedure for producing a microneedle array.

Next, as illustrated in FIG. 10, a polymer-dissolved solution 132 is supplied onto the needle-like depressions 12 and the region 14 where the needle-like depressions 12 have been formed, and the needle-like depressions 12 are filled with the polymer-dissolved solution 132 (polymer-dissolved solution filling step). As the polymer-dissolved solution 132, the above-described base material liquid may be used or a polymer-dissolved solution containing a drug in the base material liquid may be used. The supply of the polymer-dissolved solution 132 can be performed in the same manner as the above-described supply of the base material liquid illustrated in FIGS. 3 and 4. That is, the polymer-dissolved solution 132 is supplied onto the mold 10 so as to cover at least a part of the stepped portion 16, and the polymer-dissolved solution 132 is fixed at the contact position 17 by using the contraction due to the surface tension.

Figure 11:
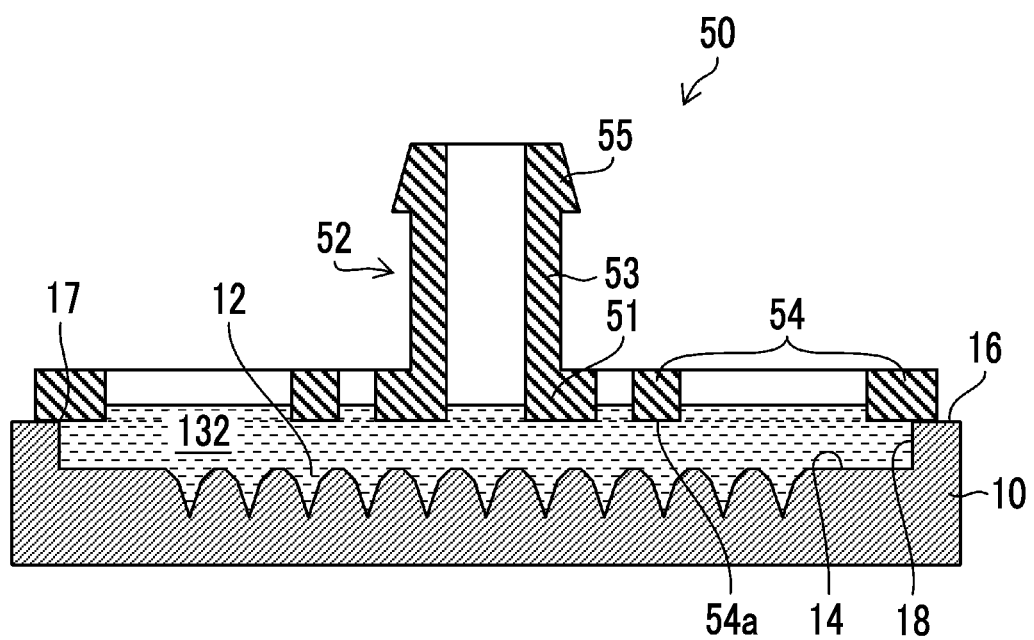
FIG. 11 is another step view illustrating a procedure for producing a microneedle array.

Next, as illustrated in FIG. 11, the support member 50 is placed on the stepped portion 16 of the mold 10 from above the polymer-dissolved solution 132 supplied on the mold 10 (support member placing step). Since the polymer-dissolved solution 132 is held at a position higher than the stepped portion 16 due to the surface tension, at least a part of the beam portion 54, that is, the lower end 54a of the beam portion 54 can be buried by placing the support member 50 on the stepped portion 16 of the mold 10.

Figure 12:
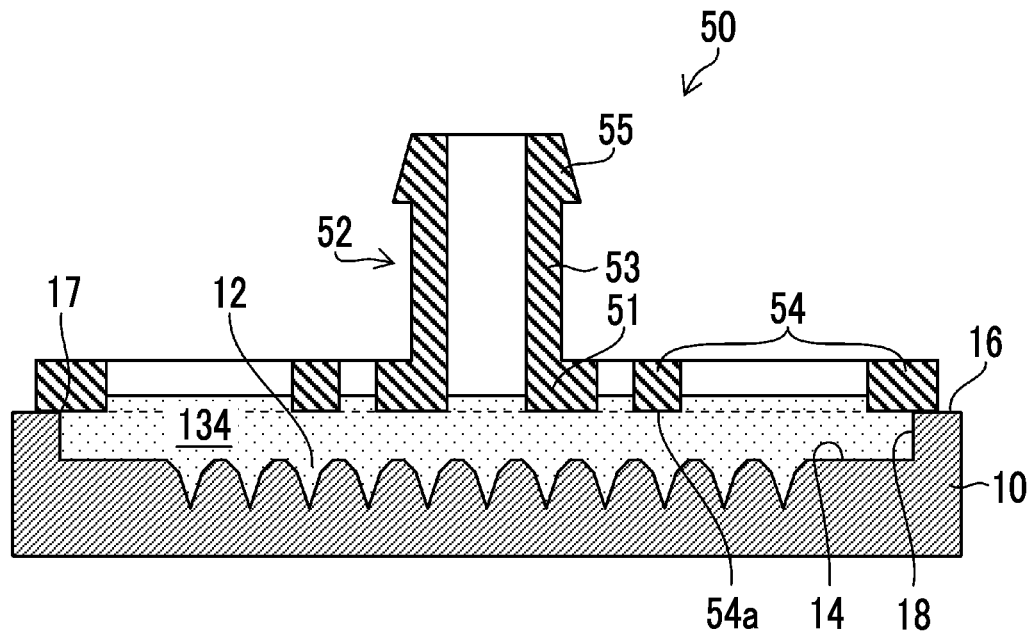
FIG. 12 is another step view illustrating a procedure for producing a microneedle array.

Next, as illustrated in FIG. 12, the polymer-dissolved solution 132 is dried and solidified in a state in which the support member 50 is placed on the stepped portion 16 of the mold 10 (polymer layer Miming step). In this manner, as illustrated in FIG. 12, the microneedle array 140 in which the polymer layer 134 and the support member 50 are integrally molded is formed. Even in the present embodiment, since the polymer-dissolved solution 132 can be dried from the gap between the beam portions 54, it is possible to prevent the delay in drying. Further, since the beam portion 54 can be deformed by following the contraction of the polymer-dissolved solution 132, it is possible to prevent breakage of the polymer layer 134 in a case of drying the polymer-dissolved solution 132.

Figure 13:
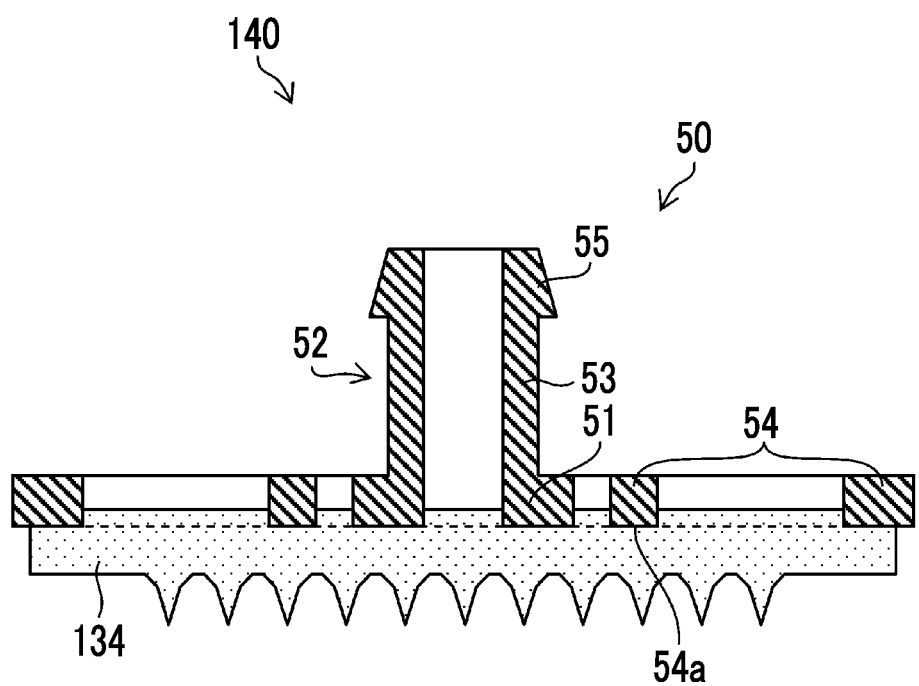
FIG. 13 is another step view illustrating a procedure for producing a microneedle array.

Finally, as illustrated in FIG. 13, the microneedle array 140 is produced by peeling the dried microneedle array 140 off from the mold 10.

[Other Embodiments of Support Member]

Figure 15:
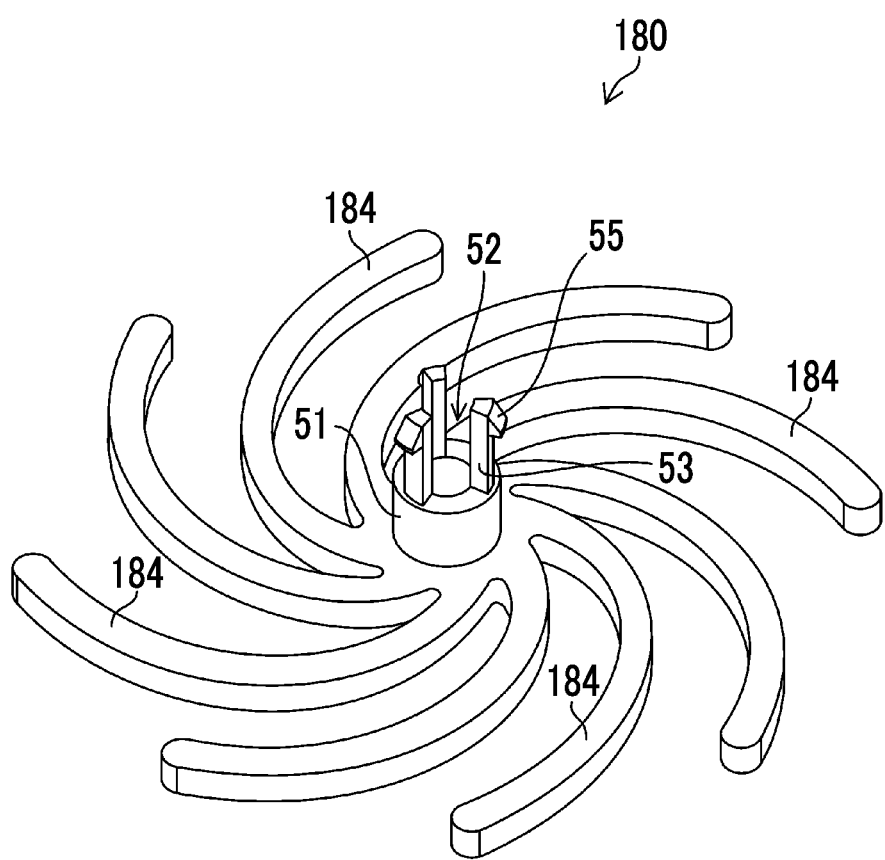
FIG. 15 is a perspective view illustrating still another example of the support member.
Figure 16:
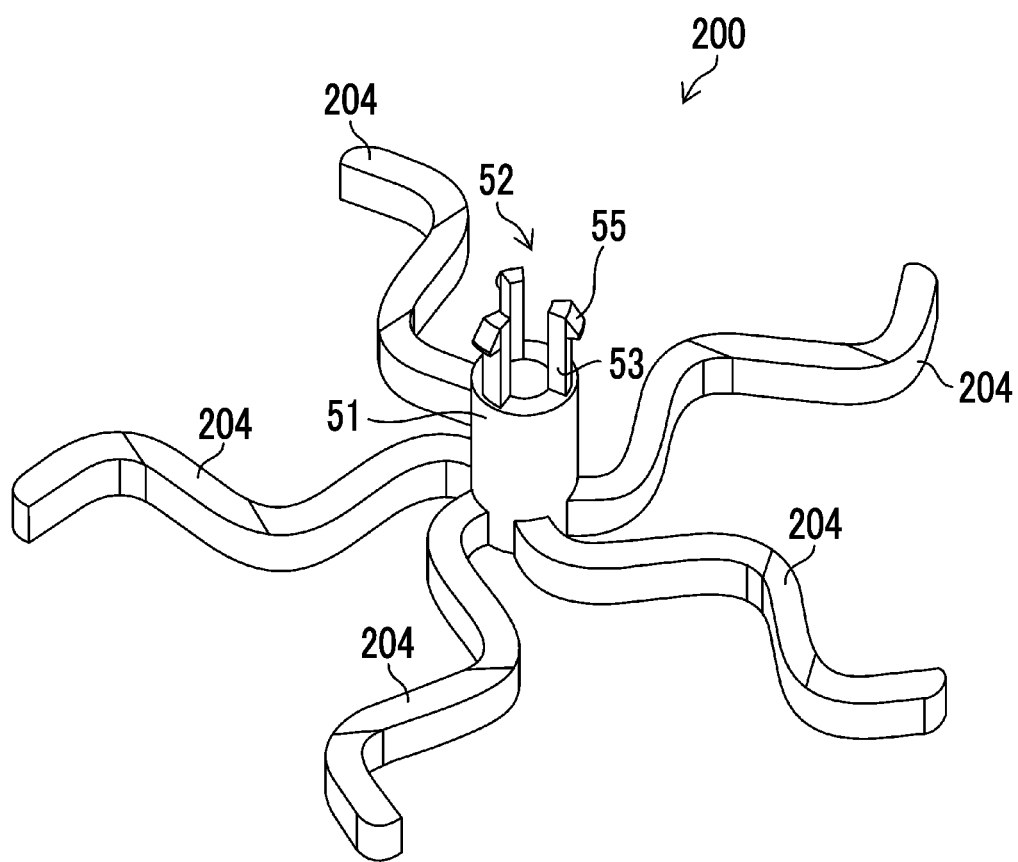
FIG. 16 is a perspective view illustrating still another example of the support member.
Figure 17:
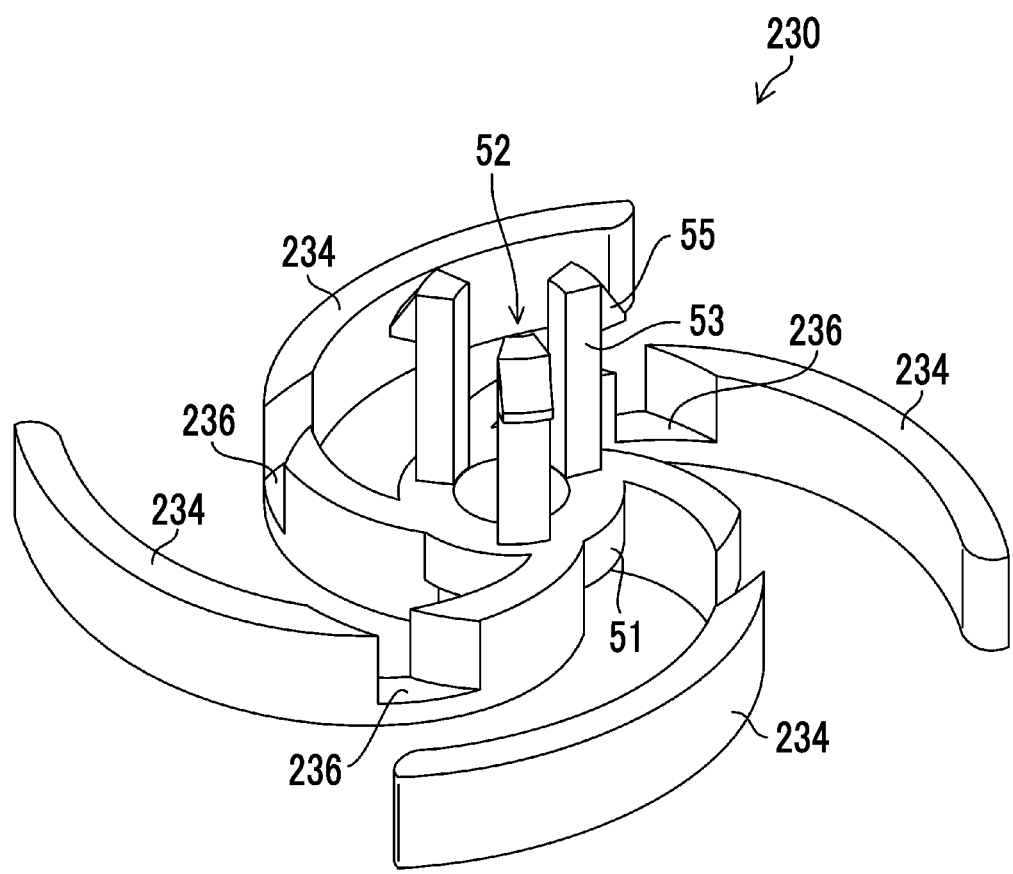
FIG. 17 is a perspective view illustrating still another example of the support member.
Figure 18:
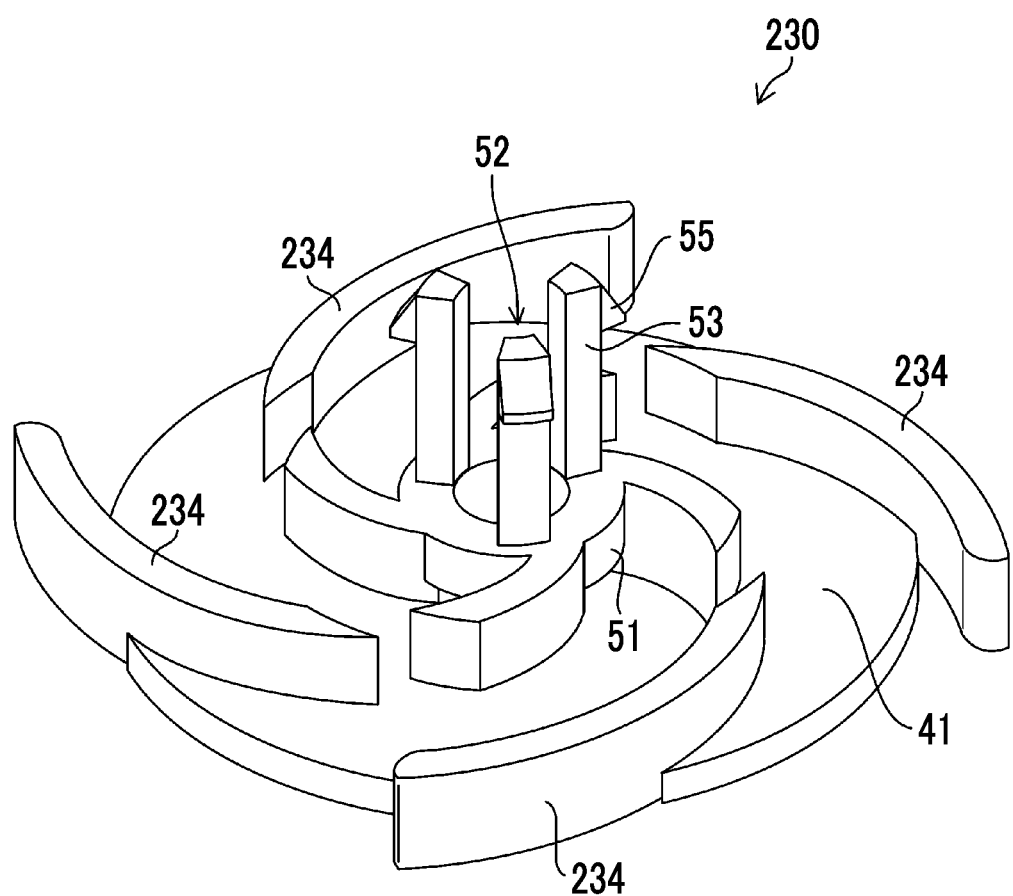
FIG. 18 is a perspective view illustrating a microneedle array produced using the support member illustrated in FIG. 17.

FIGS. 14 to 17 are perspective views illustrating other embodiment of the support member, and FIG. 18 is a perspective view illustrating a microneedle array produced using the support member illustrated in FIG. 17.

Figure 14:
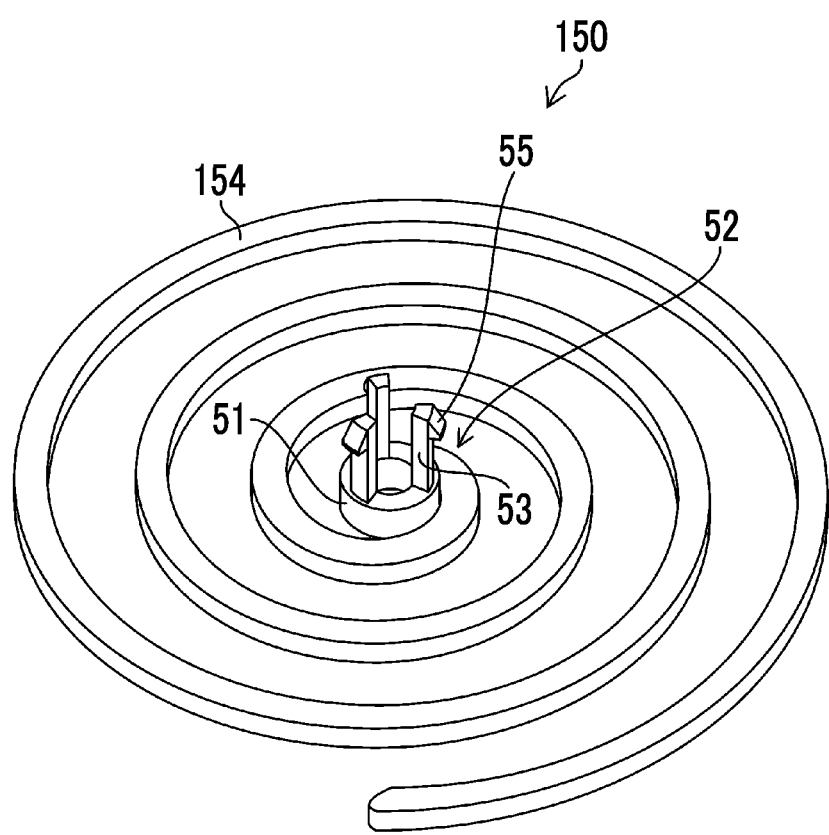
FIG. 14 is a perspective view illustrating another example of the support member.

In a support member 150 illustrated in FIG. 14, one beam portion 154 is provided in the gripping portion 52, and the beam portion 154 is formed in a spiral shape.

A support member 180 illustrated in FIG. 15 is formed of eight beam portions 184 while the support member 50 illustrated in FIG. 6 is formed of four beam portions 54.

In a support member 200 illustrated in FIG. 16, a beam portion 204 extending from the gripping portion 52 has a plurality of inflection points and extends outward while changing the curving direction.

Even in the support member illustrated in FIGS. 14 to 16, the beam portion can be deformed in the contraction direction of the base material liquid 102 in a case of drying the base material liquid 102 by forming the beam portion in a curved shape, and thus the beam portion can be made to follow the contraction direction of the base material liquid.

Further, the support member 230 illustrated in FIG. 17 has a cut-out portion 236 in a beam portion 234. In the cut-out portion 236, the notch is formed in another direction opposite to the one direction in which the gripping portion 52 extends. By providing the cut-out portion 236, the cut-out portion 236 can be buried in the base material liquid 102 in a case of placing the support member 230 on the stepped portion 16 of the mold 10. As illustrated in FIG. 18, the support member 230 and the sheet portion can be molded more integrally with each other by burying depressions.

[Microneedle Array Unit]

Next, a microneedle array unit having a microneedle array will be described. The microneedle array unit has a microneedle array and a container that accommodates the microneedle may. Further, the container comprises an accommodation portion that accommodates the microneedle array, and a lid member that seals an opening provided in the accommodation portion. In the microneedle array unit, a part of the container is deformed by applying an external force from a side opposite to the opening, the microneedles are pushed out of the container, and the microneedle array is pressed by the deformed container.

Figure 19:
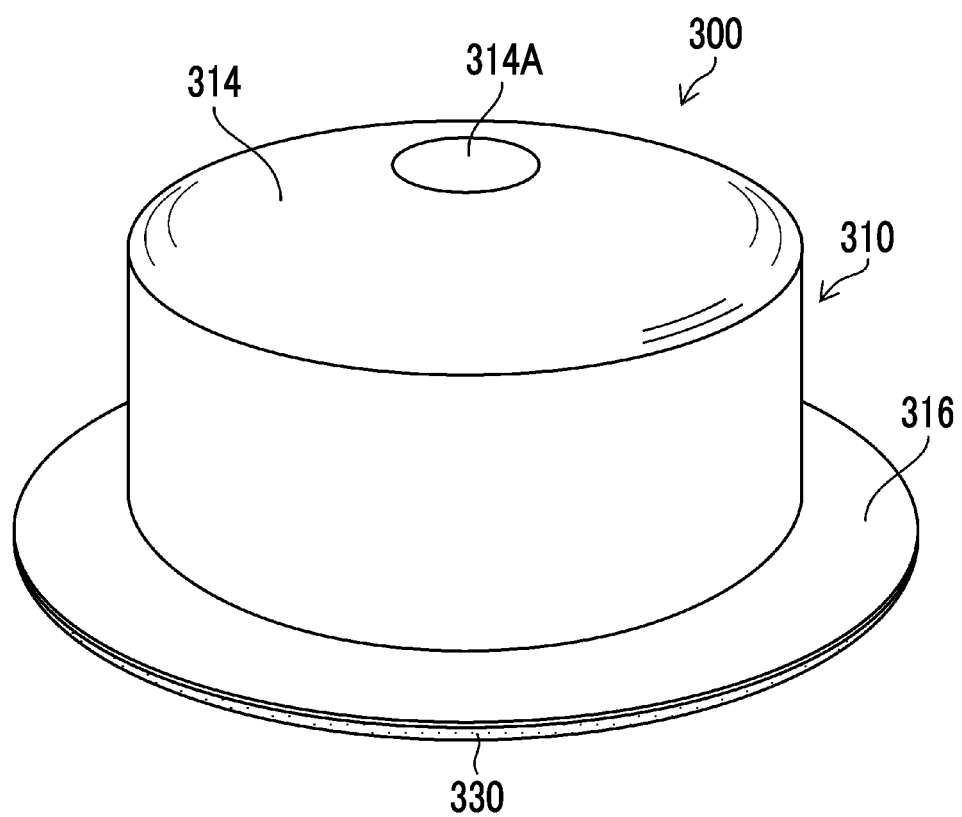
FIG. 19 is a perspective view illustrating a microneedle array unit.
Figure 20:
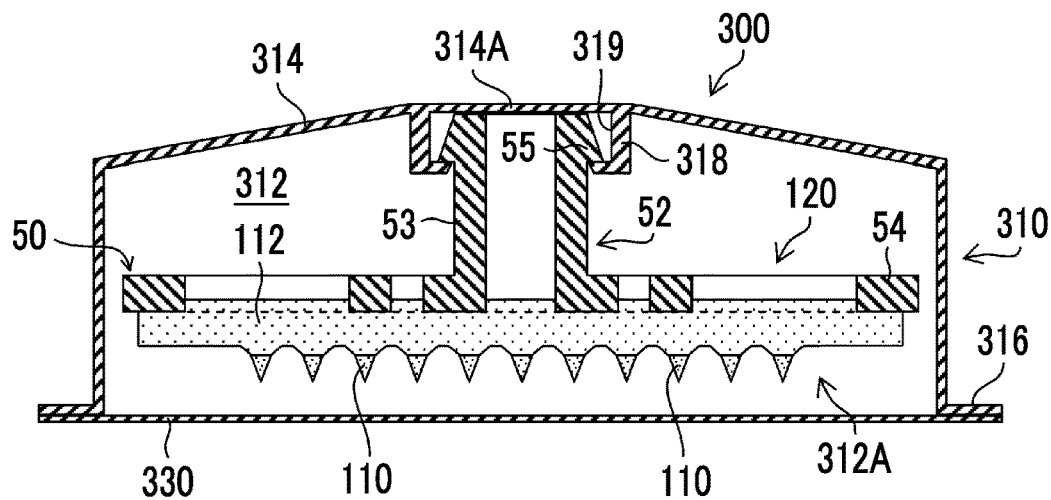
FIG. 20 is a cross-sectional view of the microneedle array unit illustrated in FIG. 19.

FIG. 19 is a perspective view of the microneedle array unit, and FIG. 20 is a cross-sectional view of the microneedle array unit illustrated in FIG. 19.

As illustrated in FIGS. 19 and 20, a microneedle array unit 300 comprises a container 310. The container 310 comprises an accommodation portion 312 for accommodating the microneedle array 120, a deformable portion 314 integrated with the accommodation portion 312, and a flange portion 316 which is integrated with the accommodation portion 312 and extends outward from the periphery of an opening 312A.

The accommodation portion 312, the deformable portion 314, and the flange portion 316 of the container 310 have a circular shape in plan view. However, the shapes of the accommodation portion 312, the deformable portion 314, and the flange portion 316 are not limited thereto. It is preferable that the shapes and the sizes of the accommodation portion 312 and the deformable portion 314 correspond to the shape and size of the microneedle array 120. The flange portion 316 is a portion that comes into contact with the skin at the time of puncturing the skin with the microneedle array 120. The flange portion 316 is provided on the entire periphery of the accommodation portion 312. The entire periphery indicates that the flange portion 316 surrounds the entire circumference of the accommodation portion 312.

As illustrated in FIG. 20, the accommodation portion 312 has an internal space defined by an inner wall and the opening 312A. The opening 312A of the accommodation portion 312 is sealed by the lid member 330. The accommodation portion 312 is sealed by bringing the periphery of the lid member 330 into contact with the flange portion 316.

The deformable portion 314 is disposed on a side opposite to the microneedle array 120 in the accommodation portion 312 with respect to the opening 312A and is integrated with the accommodation portion 312. In the embodiment, for example, the deformable portion 314 is formed in a convex shape with a vertex 314A separated from the microneedle array 120. The convex shape indicates that the vertex 314A is not positioned in the internal space of the accommodation portion 312. The term "integrated" indicates a state where the accommodation portion 312 is connected with the deformable portion 314. For example, in a case where the accommodation portion 312 is integrated with the deformable portion 314, this integration can be achieved by separately molding the accommodation portion 312 and the deformable portion 314, fitting the accommodation portion 312 and the deformable portion 314 to each other, and welding the accommodation portion and the deformable portion. In a case where the accommodation portion 312 is integrally molded with the deformable portion 314, the integration may be carried out before or after the accommodation of the microneedle array 120 in the accommodation portion 312. In the case where the accommodation portion 312 is integrated with the deformable portion 314, the integration can be realized by integrally molding the accommodation portion 312 and the deformable portion 314. However, the present invention is not limited to these methods.

The deformable portion 314 may have a frustum shape. In the embodiment, the deformable portion has a conical shape. Further, the deformable portion may have a cone shape such as a pyramid shape, and a frustum shape or a dome shape can be employed. Further, the deformable portion 314 may have, for example, an internal space, and the internal space of the deformable portion 314 can communicate with the internal space of the accommodation portion 312. The accommodation portion 312 has a structure closed by the deformable portion 314 on a side opposite to the opening 312A.

The flange portion 316 is integrated with the accommodation portion 312 and comes into contact with the skin as described below. In the embodiment, the flange portion 316 extends outward from a position of the opening 312A of the accommodation portion 312. The flange portion 316 is formed so as to be parallel to the sheet portion of the microneedle array 120. The concept of "parallel" includes parallel and substantially parallel. As described below, the shape of the flange portion 316 is not particularly limited as long as the flange portion comes into contact with the skin. In a case where the accommodation portion 312 is integrated with the flange portion 316, the same method as in the case where the accommodation portion 312 is integrated with the deformable portion 314 can be applied.

The binding portion 318 that is bound to the microneedle array 120 and fixes the microneedle array 120 to the container 310 is provided on a side of the accommodation portion 312 of the deformable portion 314. The microneedle array 120 is fixed to the container 310 by binding the binding portion 318 to the gripping portion 52 of the microneedle array 120 so that the microneedle array 120 is integrated with the container 310. According to the method of binding the binding portion 318 to the gripping portion 52, the microneedle array and the container are integrated with each other by fitting the claw portion 55 provided in the gripping portion 52 to a groove 319 provided in the binding portion 318. Further, the method of binding the binding portion 318 to the gripping portion 52 is not limited thereto. For example, the groove is provided in the gripping portion to fix the microneedle array and the container by providing the claw portion in the binding portion. The microneedle array 120 and the container 310 are fixed by fitting a member, and the safety for a living body can be ensured by not using an adhesive.

It is preferable that the container 310 constituting the microneedle array unit 300 is formed of, for example, a polyethylene resin, a polypropylene resin, or a mixture thereof. However, the present invention is not limited thereto. It is preferable that each of these materials satisfies the "Specification of Aqueous Injection Container made of Plastic (hereinafter, simply referred to as injection container grade)" of Japanese Pharmacopoeia. In addition, the container 310 may be formed of various other resin materials satisfying the same specification.

In particular, a material in which the shape is deformed at the time of the deformable portion 314 receiving an external force and the deformed shape is maintained is selected from among these materials. The material to be used is determined in consideration of the shape and thickness of the deformable portion 314, the magnitude of the external force required for deformation, and the like.

According to the microneedle array 120 of the present embodiment, packaging of the microneedle array 120 in a sterile room can be easily performed by integrally molding the support member 50 with the sheet portion 41 (base material layer 112). Since the microneedle array 120 is used by puncturing the skin, it is necessary to protect the microneedles until the skin is punctured. Further, in order to ensure the sterility of the microneedle array 120, the packaging of the microneedle array in the container 310 is performed in a sterile room, and the microneedle array is stored in the container 310 until immediately before use. In a case where the microneedle array 120 is not integrated with the support member 50, the container 310, the support member 50, and the microneedle array 120 are separately fixed in a sterile room. Therefore, it takes time to work in a sterile room. Further, members for fixing the support member 50 and the microneedle array 120 are also required. By integrally molding the support member 50 with the sheet portion 41 and by fixing the support member 50 to the container 310, the microneedle array 120 can be fixed to the container 310, and the packaging step in a sterile room can be simplified. Further, the number of members for fixing the support member 50 and the microneedle array 120 can be reduced.

Figure 21:
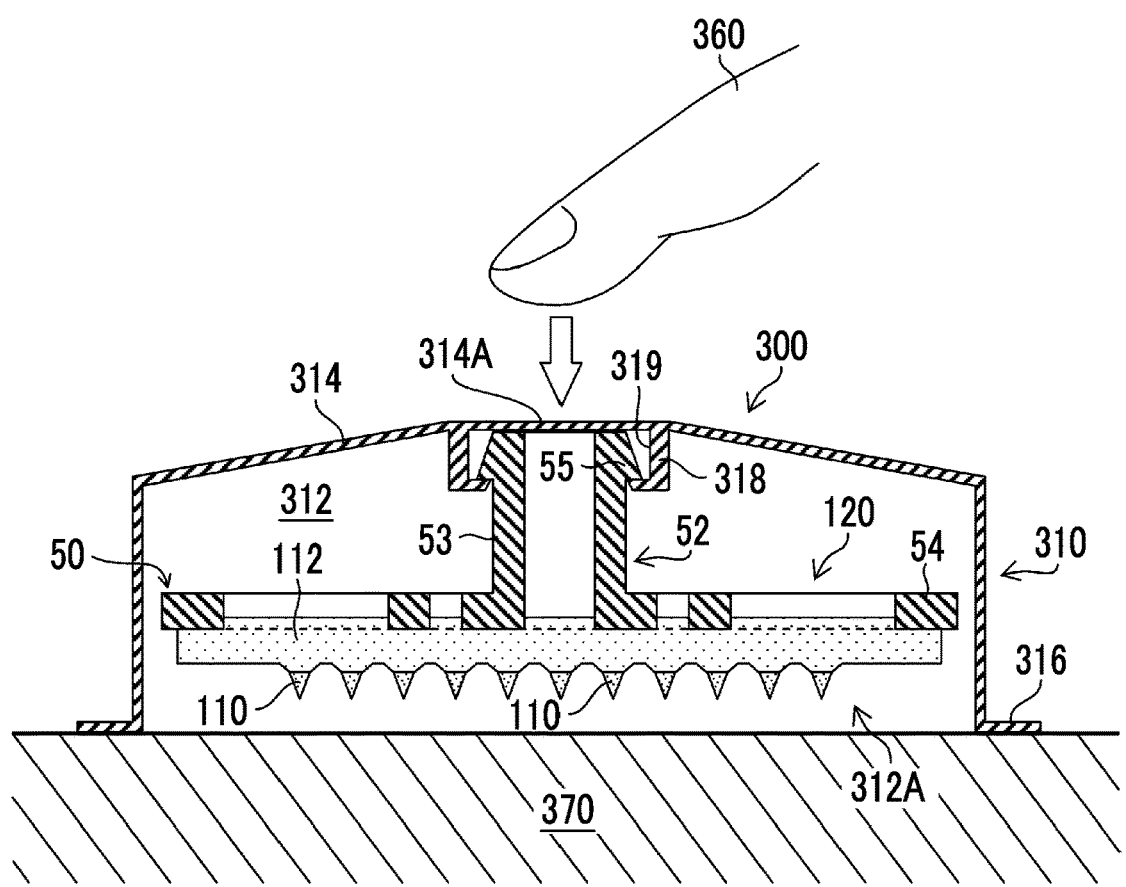
FIG. 21 is a view for describing a step of puncturing the skin with a microneedle array.

Next, a step of puncturing the skin with the microneedle array 120 using the microneedle array unit 300 will be described with reference to FIGS. 21 to 23. FIGS. 21 to 23 are cross-sectional views of the microneedle array unit 300 illustrating the step of puncturing the skin with the microneedle array 120.

First, the lid member 330 that seals the opening 312A of the accommodation portion 312 is peeled off from the container 310. The needle-like protrusions 44 of the microneedle array 120 are protected from damage because of the lid member 330. It is preferable that the lid member 330 has a knob in order to facilitate the peeling.

Next, the container 310 is positioned on a skin 370 as illustrated in FIG. 21. The opening 312A of the accommodation portion 312 is positioned toward the skin 370, and the needle-like protrusions 44 of the microneedle array 120 are oriented toward the skin 370. The flange portion 316 extending outward from the accommodation portion 312 is brought into contact with the skin 370. A finger 360 is positioned at a position separated from the deformable portion 314 in order to apply an external force to the deformable portion 314 in a direction of the opening 312A. The microneedle array 120 is supported by fitting the binding portion 318 of the container 310 and the gripping portion 52 of the support member 50 and is positioned in the internal space of the accommodation portion 312.

After the container 310 is positioned on the skin 370, the deformable portion 314 is pressed toward the skin 370 by the finger 360. The deformable portion 314 is deformed by receiving an external force in a direction of the opening 312A. As illustrated in FIG. 22, the deformable portion 314 is deformed by an external force, and the deformed shape of the deformable portion 314 is maintained even after the external force is removed. The deformable portion 314 which has been deformed presses the microneedle array 120 toward the skin 370.

As described above, the microneedle array 120 is fixed to the container 310 by fitting the binding portion 318 provided on the deformable portion 314 and the gripping portion 52 provided on the support member 50. Therefore, by pressing the deformable portion 314, the microneedle array 120 is pushed out of the accommodation portion 312 through the gripping portion 52 in a state where the microneedle array 120 is fixed to the container 310. The microneedle array 120 passes through the opening 312A, and the needle-like protrusions 44 of the microneedle array 120 puncture the skin 370.

After the puncture, since the microneedle array 120 is pressed by the deformable portion 314 of the container 310 until the drug of the microneedle array 120 is administered, falling of the microneedle array 120 off the skin 370 without pressing of the finger 360 is prevented.

By designing the outer diameter of the microneedle array 120, that is, the beam portion 54 of the support member 50 to be slightly smaller than the inner diameter of the accommodation portion 312, it is possible to prevent the pressed microneedle array 120 from being greatly deviated from a direction of the opening 312A. Therefore, the skin 370 can be vertically punctured by the needle-like protrusions 44 of the microneedle array 120.

Finally, the microneedle array 120 is peeled off together with the container 310 as illustrated in FIG. 23. The peeling of the microneedle array is performed after the skin 370 is punctured by the needle-like protrusions 44 of the microneedle array 120 and the time for which the drug layer 110 forming the needle-like protrusions 44 remains in the skin is elapsed. In this manner, the drug can be injected into the skin. Since the microneedle array 120 is fixed to and integrated with the container 310, the treatment can be performed without separating the microneedle array 120 and the container 310 from each other even at the time of puncturing the skin and peeling the microneedle array from the skin. Therefore, separate disposal of the microneedle array 120 and the container 310 is not required at the time of puncturing the skin with the microneedle array 120, and the disposal can be easily carried out. Further, by disposing of the microneedle array 120 and the container 310 together, it is possible to prevent the microneedle array 120 from remaining on a patient side and improve the safety for the patient.

EXPLANATION OF REFERENCES

10: mold
12: needle-like depression
14: region where needle-like depressions have been formed
16: stepped portion
17: contact position
18: wall portion
41: sheet portion
42: one surface
42A: outer peripheral surface
42B: microneedle region
42C: imaginary line
43: other surface
44: needle-like protrusion
50, 150, 180, 200, 230: support member
51: base portion
52: gripping portion
53: rod-like portion
54, 154, 184, 204, 234: beam portion
54a: lower end
55: claw portion
102: base material liquid
110: drug layer
112: base material layer
120, 140: microneedle array
132: polymer-dissolved solution
134: polymer layer
236: cut-out portion
300: microneedle array unit
310: container
312: accommodation portion
312A: opening
314: deformable portion
314A: vertex
316: flange portion
318: binding portion
319: groove
330: lid member
360: finger
370: skin

What is claimed is:

1. A microneedle array comprising:
a sheet portion;
a plurality of needle-like protrusions arranged on one surface of the sheet portion; and
a support member formed of a gripping portion which extends in one direction and a beam portion having one end that is connected to the gripping portion,
wherein the sheet portion is an integrally molded body which is integrally molded with the support member, in which at least a part of the beam portion is buried under the other surface of the sheet portion, opposite to the one surface where the needle-like protrusions are provided,
the gripping portion is provided on the other surface of the sheet portion, and
the beam portion is deformable toward a center of the sheet portion.

2. The microneedle array according to claim 1,
wherein the beam portion is formed of two or more beams, extends in a radial direction with the gripping portion as a center, and is curved in a circumferential direction.

3. The microneedle array according to claim 2,
wherein the beam portion has a plurality of inflection points, and a curving direction of the beam portion changes.

4. The microneedle array according to claim 1,
wherein the beam portion is formed of one piece of beam and has a spiral shape with the gripping portion as a center.

5. The microneedle array according to claim 1,
wherein the beam portion has a cut-out portion, and the cut-out portion is buried inside the sheet portion.

6. A microneedle array unit comprising:
the microneedle array according to claim 1; and
a container which accommodates the microneedle array, wherein the container includes
an accommodation portion having an opening,
a deformable portion disposed on a side opposite to the opening and formed integrally with the accommodation portion,
a binding portion provided in the accommodation portion of the deformable portion and bound to the gripping portion of the microneedle array, and
a lid member which seals the opening,
the binding portion of the container is fitted and bound to the gripping portion of the microneedle array,
the deformable portion is deformed by receiving an external force in a direction of the opening and presses the microneedle array through the gripping portion,
the microneedle array is pushed out of the accommodation portion by being pressed, and the deformable portion maintains a deformed state and presses the microneedle array.

7. A support member which supports a sheet portion of a microneedle array, the support member comprising:
a gripping portion which extends in one direction; and
a beam portion having one end that is connected to a side surface of the gripping portion and curvedly extending from the gripping portion in a diametric direction and a circumferential direction,
wherein the beam portion is deformable toward the gripping portion.

8. The support member according to claim 7,
wherein the beam portion is formed of two or more beams, extends in a radial direction with the gripping portion as a center, and is curved in a circumferential direction.

9. The support member according to claim 8,
wherein the beam portion has a plurality of inflection points, and a curving direction of the beam portion changes.

10. The support member according to claim 7,
wherein the beam portion is formed of one piece of beam and has a spiral shape with the gripping portion as a center.

11. The support member according to claim 7,
wherein the beam portion has a cut-out portion toward the other direction opposite to the one direction.

12. A method of producing a microneedle array, comprising in the following order:
a polymer-dissolved solution filling step of supplying a polymer-dissolved solution to a pattern surface of a mold having needle-like depressions and filling the needle-like depressions with the polymer-dissolved solution;
a support member placing step of placing the support member according to claim 6 on the mold from above having the polymer-dissolved solution applied onto the needle-like depressions;
a polymer layer forming step of drying the polymer-dissolved solution such that a polymer layer and the support member are integrally molded with each other; and
a peeling step of peeling the polymer layer and the support member from the mold.

13. A method of producing a microneedle array, comprising in the following order:
a drug solution filling step of filling a pattern surface of a mold with a drug solution containing a drug;
a drug layer forming step of drying the drug solution to form a drug layer;
a base material liquid filling step of filling the drug layer with a base material liquid;
a support member placing step of placing the support member according to claim 6 on the mold from above the base material liquid filling the drug layer;
a base material layer forming step of drying the base material liquid such that a base material layer and the support member are integrally molded with each other; and
a peeling step of peeling the drug layer, the base material layer, and the support member from the mold.

* * * * *